United States Patent
Zhang et al.

(12)

(10) Patent No.: US 6,309,816 B1
(45) Date of Patent: Oct. 30, 2001

(54) METHODS FOR DIAGNOSING CANCER BY MEASURING CREATINE KINASE

(75) Inventors: Zhen Zhang, Mt. Pleasant, SC (US); Stephen D. Barnhill, Savannah, GA (US); Ramananda Madyastha, Charleston, SC (US); Hong Zhang, Savannah, GA (US)

(73) Assignee: Horus Therapeutics, Inc., Hilton Head, SC (US)

( * ) Notice: Subject to any disclaimer, the term of this patent is extended or adjusted under 35 U.S.C. 154(b) by 0 days.

(21) Appl. No.: 09/060,703

(22) Filed: Apr. 15, 1998

Related U.S. Application Data

(60) Provisional application No. 60/044,112, filed on Apr. 16, 1997, now abandoned.

(51) Int. Cl.[7] ............................. C12Q 1/00; G01N 33/53; G01N 33/573
(52) U.S. Cl. ................................ 435/4; 435/7.1; 435/7.4; 435/7.9
(58) Field of Search .................................. 435/4, 7.1, 7.4, 435/7.9

(56) References Cited

U.S. PATENT DOCUMENTS 5,769,074 * 6/1998 Barnhill et al. .

FOREIGN PATENT DOCUMENTS

| WO 96/26442 | 8/1986 | (WO) . |
| WO 97/05553 | 2/1997 | (WO) . |
| WO 97/29199 | 8/1997 | (WO) . |

OTHER PUBLICATIONS

Zarghami, Nosratollah et al., "Quantification of Creatine Kinase BB Isoenzyme in Tumor Cytosols and Serum with an Ultrasensitive Time–Resolved Immunofluorometric Technique," *Clinical Biochemistry,* vol. 28, No. 3, pp. 243–253 (1995).

Feld, Ronald D. et al., "The Presence of Creatine Kinase BB Isoenzyme in Patients with Prostatic Cancer," *Clinica Chimica Acta,* vol. 100, No. 3, pp. 267–273 (1980).

Barnhill et al (J. Clin. Ligand Assay, 21:18–23), 1998.*

Duranyildiz et al (J. Tumor Marker Oncol, 14:39–46), 1999.*

* cited by examiner

*Primary Examiner*—Susan Ungar
(74) *Attorney, Agent, or Firm*—Kilpatrick Stockton LLP

(57) ABSTRACT

The diagnostic method of the present invention provides a method of diagnosing prostate cancer by measuring the concentration of prostate specific antigen and creatine kinase enzyme activity. A mathematical relationship between the two concentrations is then determined. If the prostate specific antigen concentration in the blood is normal or near normal and the creatine kinase enzyme value is lower than normal, than there is a high likelihood that the patient has prostate cancer. The present invention also includes the measurement of creatine kinase enzyme inhibitor in the serum of a patient to determine if the patient has a high likelihood of cancer.

7 Claims, 4 Drawing Sheets

METHODS FOR DIAGNOSING CANCER BY MEASURING CREATINE KINASE

PRIOR RELATED APPLICATIONS

This application claims priority to U.S. provisional patent application Ser. No. 60/044,112 filed on Apr. 16, 1997 now abandoned.

TECHNICAL FIELD

The present invention is in the field of diagnostic methods and, more specifically, the present invention is related to the diagnosis of cancer.

BACKGROUND OF THE INVENTION

The prostate gland is a site of significant pathology affected by conditions such as benign growth (BPH), neoplasia (prostatic cancer) and infection (prostatitis). Prostate cancer represents the second leading cause of death from cancer in man. However, prostate cancer is the leading site for cancer development in men. The difference between these two facts relates to prostatic cancer occurring with increasing frequency as men age, especially in the ages beyond 60, at a time when death from other factors often intervenes. Also, the spectrum of biologic aggressiveness of prostatic cancer is great, so that in some men following detection the tumor remains a latent histologic tumor and does not become clinically significant, whereas in other patients it progresses rapidly, metastasizes and kills the man in a relatively short 2 through 5 year period.

Prostate specific antigen (PSA) is a tissue specific glycoprotein which can only be found in the prostate gland and its secretions. Because of the tissue specificity of PSA, it is well known to be a unique indicator for the prostate function as described by Hara, M., et al., *Two prostate specific antigens gamma-semino-protein and beta-microsemino-protein,* J. Lab. Clin. Med. 1989; 113: 541–48. PSA is therefore a particularly useful indicator in controlling patients after radical prostatectomy, and determining whether they suffer any further appearance of their prostate cancer because the operative intervention should have removed the entire prostate tissue and therewith also the possible source for releasing prostate specific antigen. In patients with a prostate cancer, in whom, through histological examination the cancer has been proven to be limited to the prostate organ, the value of PSA after radical prostatectomy falls under the detection level of the presently available immunoassays in 80–92% of the cases. A further increase in the PSA value is the earliest available indicator for a further appearance of the cancer after a complete prostatectomy.

Although the detection of PSA has certainly proved to be an indicator of the presence of prostate cancer, there is an unacceptable number of patients who have normal or near normal PSA serum levels but have prostate cancer. In addition, there are a large number of patients with abnormally high PSA serum levels that have a benign tumor.

Recently, it has been reported that measuring the ratio of free PSA to bound PSA in the serum is a more accurate method of diagnosing prostate cancer. However, this method, while reportedly more accurate in diagnosing prostate cancer than free PSA only, still misses a high number of patients with prostate cancer.

What is needed is a method that can be easily administered and accurately diagnose or provide prognosis for the presence of prostate cancer, preferably in its early stages.

SUMMARY OF THE INVENTION

The diagnostic method of the present invention provides a method of diagnosing prostate cancer by measuring the concentration of prostate specific antigen and creatine kinase enzymatic activity. A mathematical relationship between the two concentrations is then determined. It has been determined that if the prostate specific antigen concentration in the blood is normal or near normal and the creatine kinase value is lower than normal, than there is a high likelihood that the patient has prostate cancer.

The present invention also comprises an inhibitor of creatine kinase that is present in the blood of a patient with cancer, especially prostate cancer. It has been found that if a patient has cancer, the creatine kinase concentration as measured by electrophoresis is normal. If the creatine kinase is measured by assaying enzymatic activity, the creatine kinase enzymatic activity will be abnormally low indicating the presence of an inhibitor that is associated with the cancer.

As part of the present invention, another way of diagnosing cancer in a patient, especially prostate cancer, is to measure creatine kinase by electrophoresis and to measure creatine kinase enzymatic activity. If the concentration of creatine kinase by electrophoresis is higher than the concentration of creatine kinase enzymatic activity, then the patient has a high likelihood of having cancer.

The present invention also includes a diagnostic kit for the diagnosis of prostate cancer in a male human comprising a means for measuring the concentration of creatine kinase in the serum of the male human and a means for measuring the concentration of prostate specific antigen in the serum of the male human.

The present invention includes a diagnostic kit for measuring the concentration of the creatine kinase inhibitor that is associated with the cancer.

The diagnostic method of the present invention provides a method of easily and quickly diagnosing prostate cancer in men without having to resort to painful biopsies. Because the two proteins are already commonly measured in routine physicals, there is no need to introduce new tests into the physicians' standard battery of tests.

Accordingly, it is an object of the present invention to provide a diagnostic method that will accurately detect prostate cancer.

It is another object of the present invention to provide a method for detecting prostate cancer that uses commonly performed blood tests.

It is yet another object of the present invention to provide a method for diagnosing prostate cancer in patients with normal PSA levels.

These and other objects, features and advantages of the present invention will become apparent after a review of the following detailed description of the disclosed embodiments.

DETAILED DESCRIPTION

Figure 1:
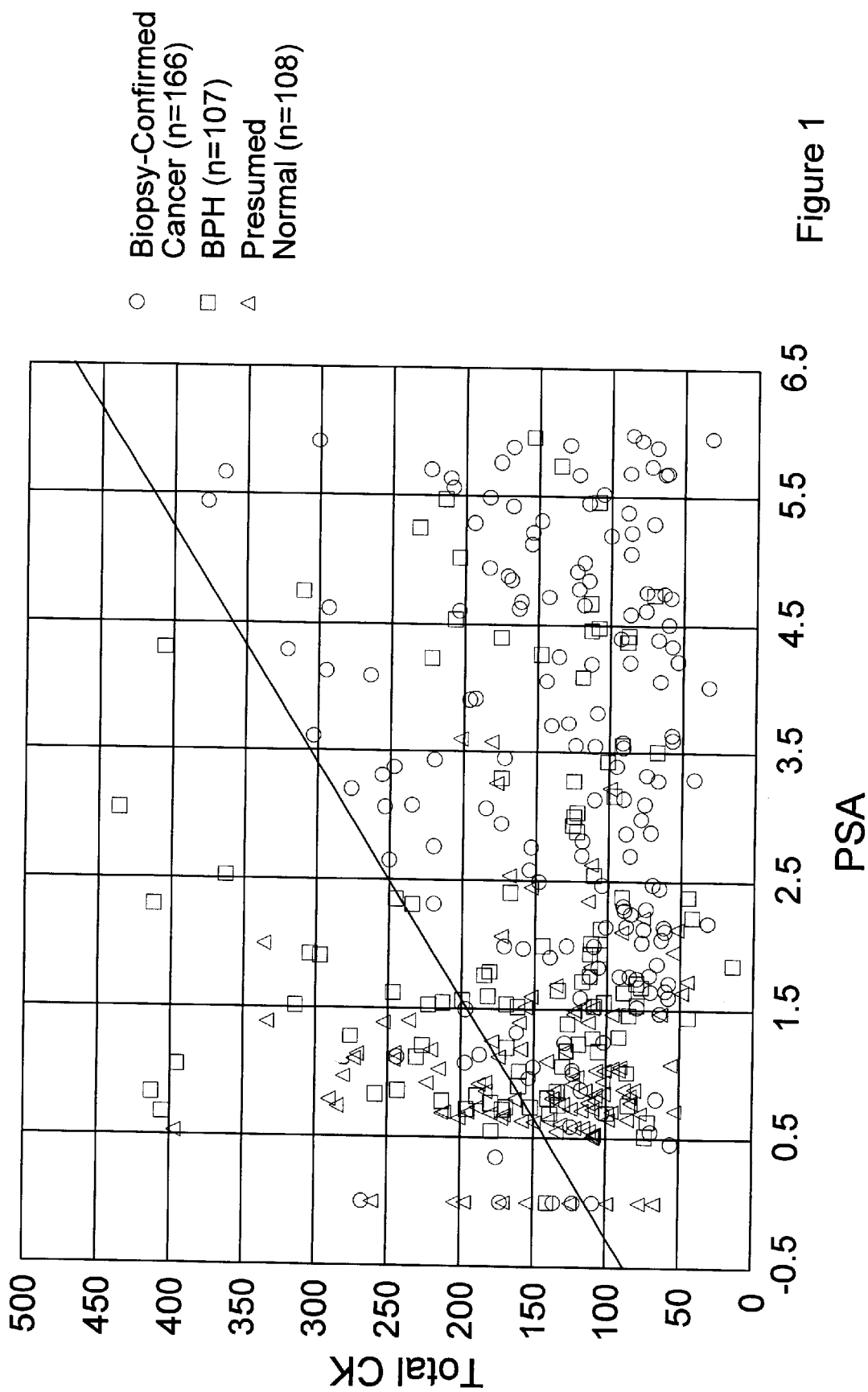
FIG. 1 is a scatter plot of 381 cases according to PSA and total CK.

The diagnostic method of the present invention provides a method of diagnosing prostate cancer by measuring the concentration of prostate specific antigen (PSA) and creatine kinase (CK). A mathematical relationship between the two concentrations is then determined. It has been determined that if the PSA concentration in the blood is normal or near normal and the CK value is lower than normal, than there is a high likelihood that the patient has prostate cancer.

In prostate cancer cells, a specific protein that is made in very high concentrations is prostate specific antigen (PSA). The protein has been characterized and has been used to follow response to therapy. With the development of cancer the normal architecture of the prostate gland becomes altered, including loss of the normal duct structure for the removal of secretions and thus the secretions reach the serum. Measurements of the serum concentration of PSA have now found widespread use in monitoring of patients with prostate cancer, although increased serum concentrations of PSA have also been reported in benign prostatic hyperplasia and secondary to surgical trauma of the prostate.

However, as stated above, the measurement of the serum concentration of PSA has proven to be a poor diagnostic or prognostic for the presence of prostate cancer. Recently, it has been reported that there is a "bound" PSA in the serum and that the ratio of the concentrations of free to bound PSA in the serum can be useful in diagnosing the presence of prostate cancer (e.g., U.S. Pat. No. 5,501,983 to Lilja et al.).

Creatine kinase (CK) is also referred to as adenosine-triphosphate (ATP)-creatine-N-phosphotransferase. It catalyzes the reversible reaction between creatine phosphate and adenosine diphosphate (ADP) to produce ATP. The ATP produced in this reaction is subsequently used to phosphorylate glucose to produce glucose-6-phosphate (G-6-P) in the presence of hexokinase. G-6-P is then oxidized by glucose-6-phosphate dehydrogenase (G-6-PDH) with the concomitant reduction of NAD to NADH. Creatine kinase is dimeric and consists of 40,000 Dalton subunits which combine to form three active hybrids: MM, MB and BB. The highest creatine kinase activities are found in skeletal muscle, myocardium and brain tissue. It is also present in the smooth muscle of the colon, small intestine, uterus, prostate, lungs and kidney.

In the diagnostic method of the present invention, it has been unexpectedly determined that the relationship between serum creatine kinase and PSA is an excellent indicator of the presence of prostate cancer. For example, if the PSA is normal, e.g., less then 6.5, and the CK as measured by enzymatic activity is lower than normal, e.g., less then 40, than the patient has a high likelihood of having cancer. As used herein, PSA is gamma-semino-protein, beta-microsemino-protein, variants thereof, or combinations thereof.

It is to be understood that the present invention can be used to diagnose cancers other than prostate cancer, i.e., when the CK is low and there are other indications that there may be a cancer in the patient, there is a high likelihood that the patient may have cancer.

As used herein, a sample includes but is not limited to biological fluids such as blood, serum, plasma, urine, prostatic secretions, seminal fluid, ejaculate, cells, cell extracts, cell culture fluid, tissue extracts, variants thereof, or combinations thereof.

The present invention also includes the assay of an inhibitor of CK. One method of assaying for the presence of the inhibitor is to measure CK by electrophoresis, which measures the presence of the protein, to measure CK in the same patient blood by measuring CK enzymatic activity, and then to compare the two values. If the concentration of CK as measured by enzymatic activity is lower than the concentration of CK as measured by electrophoresis, or any other method of measuring the CK protein, than there is an indication that the patient has cancer. Other methods of measuring the CK inhibitor can be used, such as by ELISA, radioimmunoassay, and the like.

The diagnostic method of the present invention is especially useful in determining the prognosis of a male patient who has prostate cancer or who has been treated for prostate cancer. By using the diagnostic method of the present invention, one avoids the use of painful and expensive biopsy procedures.

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

FIG. 1 shows a scatter plot of the 381 cases according to PSA and total CK. It is apparent that the majority of cancer cases fall in the lower-right corner of the plot (below the superimposed line), indicating that they have either a large PSA or a relatively small total CK level. The ratio of total CK over PSA would be a good measure on the "closeness" of a case point to the lower-right corner, and hence a diagnostic indicator for prostate cancer.

EXAMPLE 2

Figure 2:
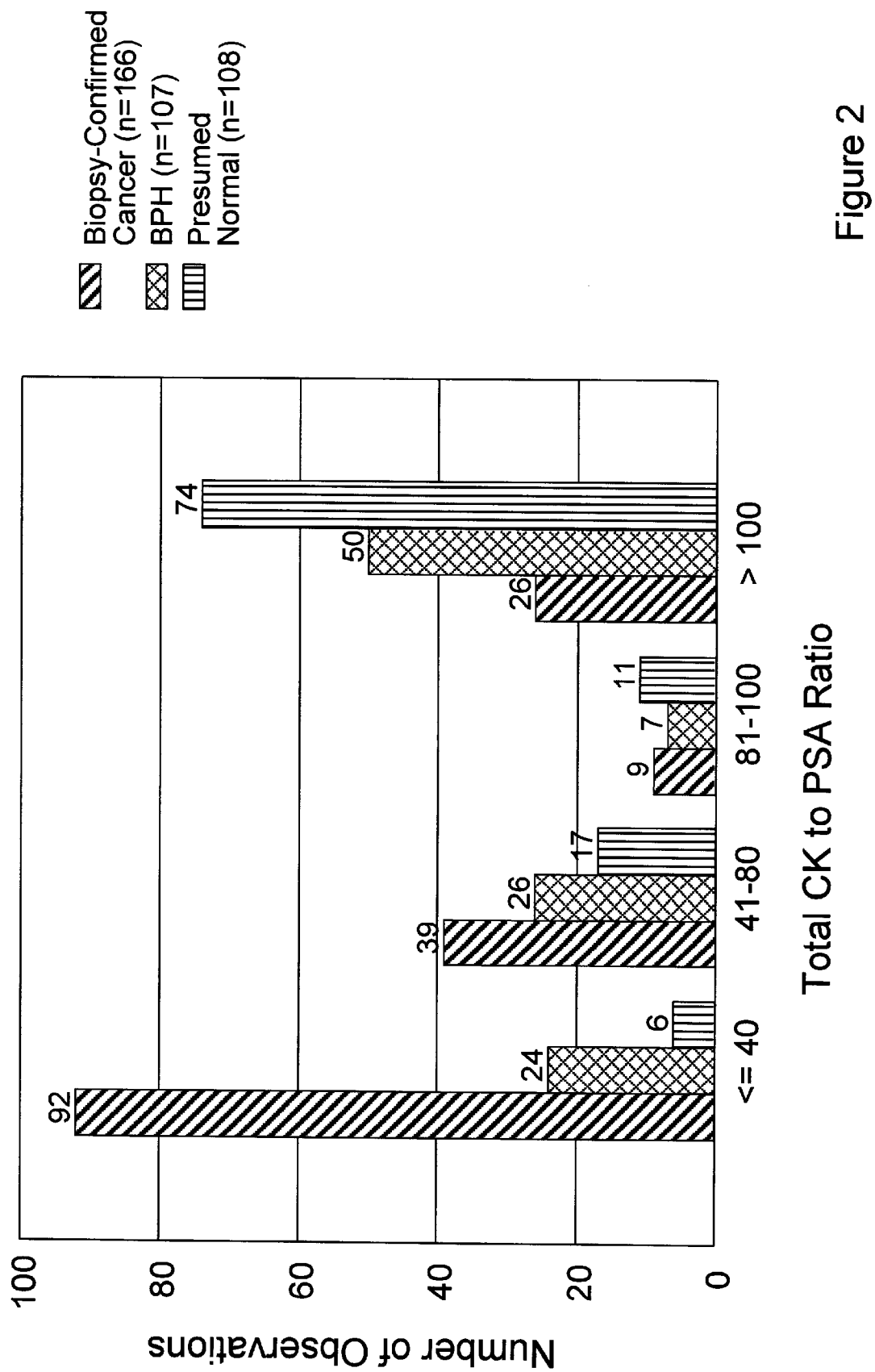
FIG. 2 is a distribution plot of total CK to PSA ratios of 381 clinical study cases.

FIG. 2 shows a distribution of total CK to PSA ratios of the 381 clinical study cases. It shows that a large proportion of the cases (92/122, or 75.4%) who have a ratio under 40 are prostate cancer patients, compared with the small percentage (26/150, or 17.3%) in the group with a ratio above 100.

EXAMPLE 3

Figure 3:
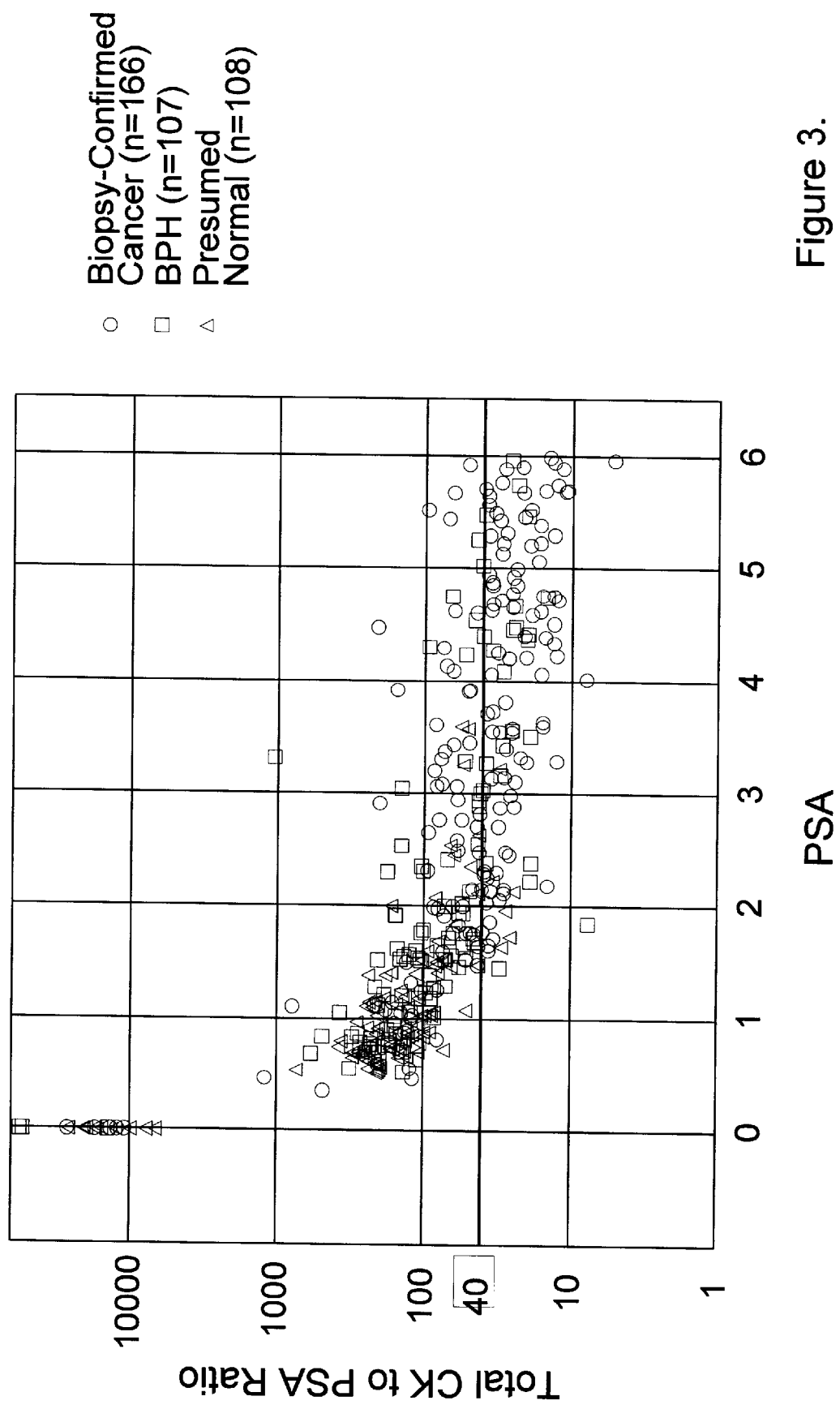
FIG. 3 is a scatter plot of the 381 cases according to PSA and the total CK to PSA ratio.

FIG. 3 shows a scatter plot of the 381 cases according to PSA and the total CK to PSA ratio. Even though PSA alone performs reasonably well in separating the cancer group from BPH and normal, a low total CK to PSA ratio is also a good indicator of prostate cancer. In fact, using the cutoff as indicated by the horizontal line at total CK to PSA Ratio=40, many cancer cases can be detected without the inclusion of too many BPH cases.

EXAMPLE 4

Figure 4:
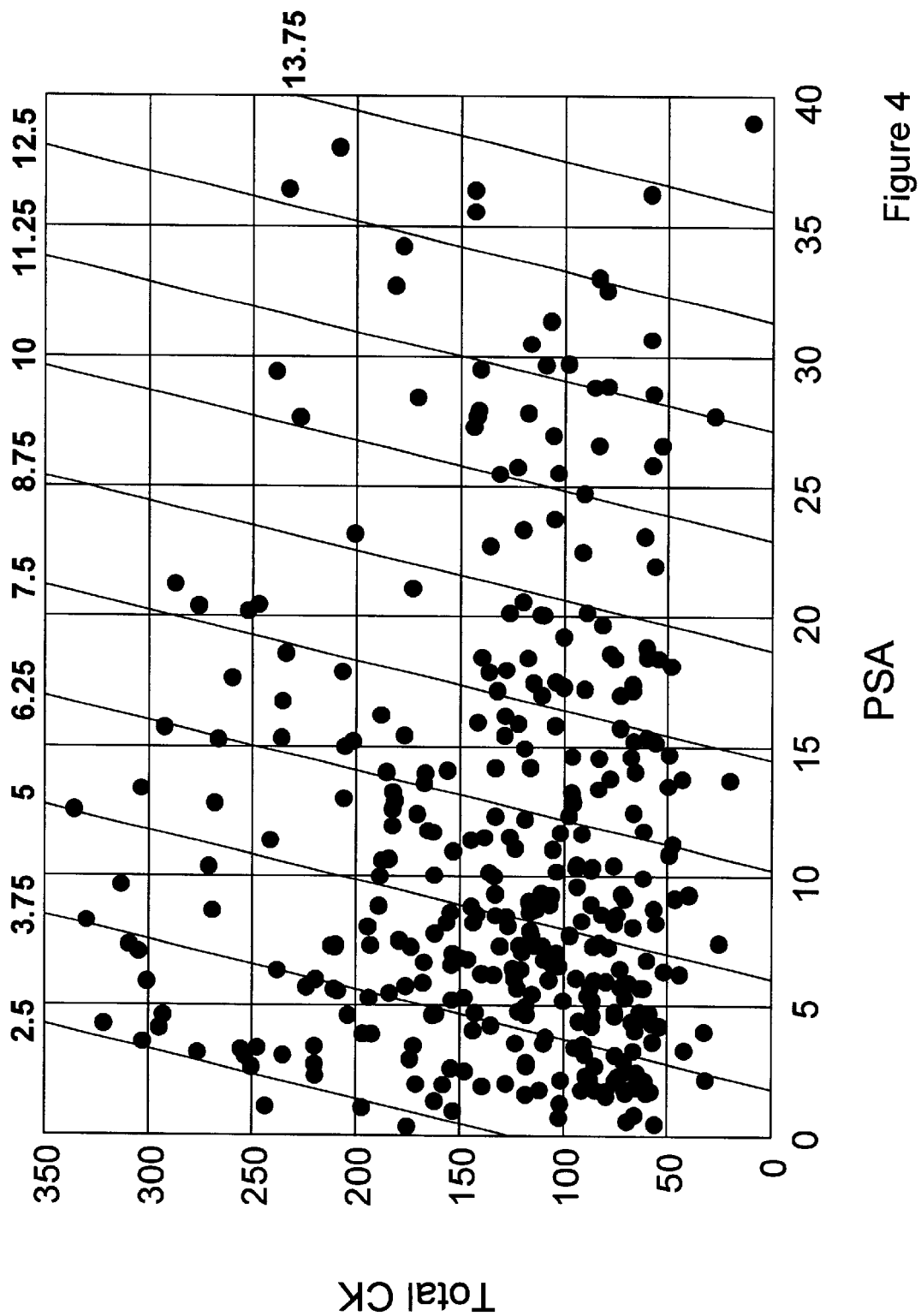
FIG. 4 is a contour plot of 403 prostate cancer cases.

FIG. 4 is a contour plot of 403 prostate cancer cases. All of the 403 patients have cancer at various stages and known tumor volume at the first site. The contour plot displays the 403 cases according to PSA and total CK. The z direction, i.e. the height of the contour line indicates the first tumor site volume. The contour lines are plotted through linear fitting. The plot shows that even though the PSA level is a much stronger indicator of tumor volumes, at a fixed PSA level, the total CK level serves as also as an indicator of the tumor volume. A smaller total CK is associated with a larger tumor volume.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims. All publications cited herein are incorporated herein by reference in their entirety.

What is claimed is:

1. A method of screening for prostate cancer in a human or an animal comprising:

measuring creatine kinase enzymatic activity in a sample from the human or animal and comparing the creatine kinase enzymatic activity to a normal control; and measuring prostate specific antigen in the sample and comparing the concentration of prostate specific antigen to a normal control;

wherein a creatine kinase enzymatic activity less than a normal control and a normal prostate specific antigen concentration is an indicator of prostate cancer.

2. The method of claim 1, wherein the creatine kinase enzymatic activity total creatine kinase enzymatic activity.

3. The method of claim 1 further comprising the step:

measuring creatine kinase protein concentration;

wherein a creatine kinase enzymatic activity less than a normal control and a normal prostate specific antigen concentration and a normal creatine kinase protein concentration is an indicator of prostate cancer.

4. The method of claim 1, wherein the sample is blood, serum, or plasma.

5. The method of claim 1, wherein the sample is serum.

6. The method of claim 3, wherein the sample is blood, serum, or plasma.

7. The method of claim 3, wherein the sample is serum.

* * * * *